United States Patent
Tak et al.

(10) Patent No.: US 7,261,952 B2
(45) Date of Patent: Aug. 28, 2007

(54) RED COLOR EMITTING COMPOUNDS FOR ORGANIC ELECTROLUMINESCENT DEVICE AND AN ORGANIC ELECTROLUMINESCENT DEVICE USING THEM

(75) Inventors: Yoon-Heung Tak, Gumi-shi (KR); Yoon-Soo Han, Kyongsangbuk-do (KR); Ki-Dong Kim, Daejeon (KR); Sang-Dae Kim, Daegu (KR); Yong-Kwan Kim, Chungcheongbuk-do (KR)

(73) Assignee: LG Electronics Inc., Seoul (KR)

( * ) Notice: Subject to any disclaimer, the term of this patent is extended or adjusted under 35 U.S.C. 154(b) by 242 days.

(21) Appl. No.: 10/745,679

(22) Filed: Dec. 29, 2003

(65) Prior Publication Data

US 2004/0137273 A1    Jul. 15, 2004

(30) Foreign Application Priority Data

Dec. 30, 2002    (KR)  ............ 10-2002-0086819

(51) Int. Cl.
*H01L 51/54*    (2006.01)
*C09K 11/06*    (2006.01)
*H05B 33/14*    (2006.01)

(52) U.S. Cl. .............. 428/690; 428/917; 313/504; 313/506; 257/102; 257/103; 564/305; 544/35; 544/102

(58) Field of Classification Search ............ 428/690, 428/917; 257/102, 103, 40; 313/504, 506; 544/102, 35; 252/102, 103; 548/440; 564/305
See application file for complete search history.

(56) References Cited

U.S. PATENT DOCUMENTS

| | | | |
|---|---|---|---|
| 6,337,167 B1 * | 1/2002 | Ichimura et al. | 430/73 |
| 6,525,212 B1 * | 2/2003 | Ichimura et al. | 558/418 |
| 2001/0033945 A1 | 10/2001 | Ishibashi et al. | 428/690 |
| 2004/0251452 A1 * | 12/2004 | Cho et al. | 252/582 |

FOREIGN PATENT DOCUMENTS

| | | |
|---|---|---|
| EP | 0 960 927 A2 | 12/1999 |
| EP | 1 073 128 A2 | 1/2001 |
| EP | 1 205 528 A1 | 5/2002 |
| JP | 11-354278 | * 12/1999 |
| JP | 2000-012225 | * 1/2000 |
| JP | 2001-307884 | * 11/2001 |

OTHER PUBLICATIONS

Tang, C.W., and S.A. VanSlyke, "Organic Electroluminescent Diodes," Applied Physics Letter v. 51, No. 12, Sep. 21, 1987, pp. 913-915.

(Continued)

*Primary Examiner*—Rena Dye
*Assistant Examiner*—Camie S. Thompson
(74) *Attorney, Agent, or Firm*—KED & Associates, LLP

(57) ABSTRACT

The present invention relates to red color emitting compounds for an organic electroluminescent device (OELD), particularly to red color emitting compounds represented by the following formula (1) having high luminescence efficiency and enhanced thermal-stability:

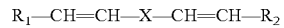

$$R_1-CH=CH-X-CH=CH-R_2$$

wherein, $R_1$, $R_2$ and X each are as defined below.

7 Claims, 1 Drawing Sheet

OTHER PUBLICATIONS

Adachi, Chihaya, Tetsuo Tsutsui, and Shogo Saito, "Organic Electroluminescent Device Having a Hole Conductor as an Emitting Layer," Applied Physics Letter v. 55, No. 15, Oct. 9, 1989, pp. 1489-1491.

Bong-Rae Cho et al.; "1,3,5-Tricyano-2,4,6-tris (vinyl) benzene Derivatives with Large Second-Order Nonlinear Optical Properties"; J. Am. Soc.; vol. 123, 2001, pp. 6421-6422; XP-002287127.

Bong Rae Cho et al., "Two Proton Absorptio Properties of 1,3,5-Tricyano-2,4,6-tris (styrl) benzene Derivatives"; J. Am. Chem. Soc.; vol. 123, 2001, pp. 10039-10045; XP002287128.

European Search Report (Aug. 27, 2004).

* cited by examiner

[FIG. 1]
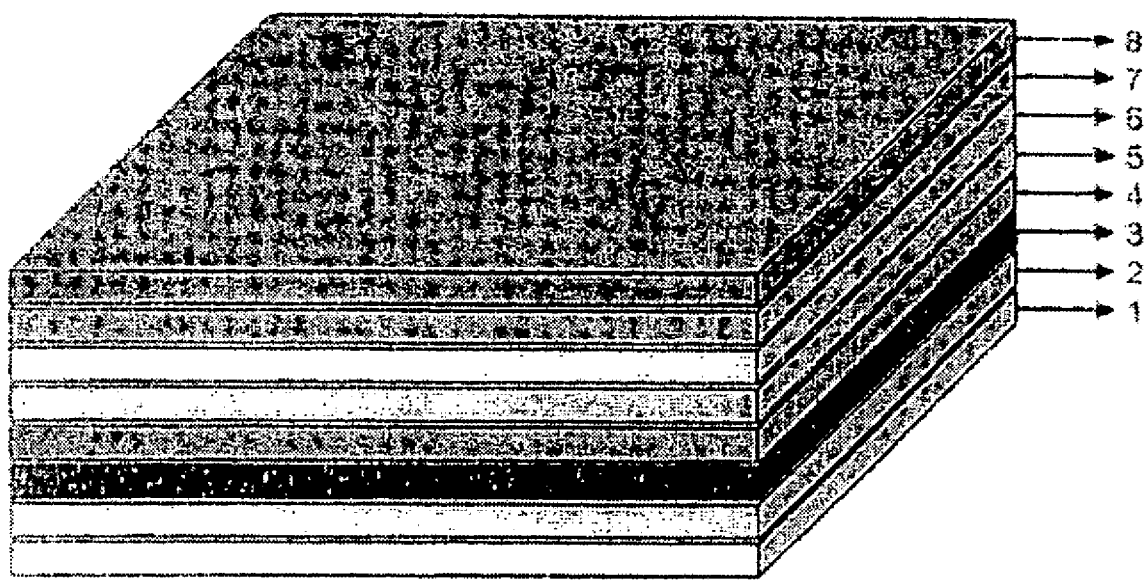

RED COLOR EMITTING COMPOUNDS FOR ORGANIC ELECTROLUMINESCENT DEVICE AND AN ORGANIC ELECTROLUMINESCENT DEVICE USING THEM

FIELD OF THE INVENTION

The present invention relates to red color emitting compounds for organic electroluminescent device (OELD), particularly to red color emitting compounds represented by the following formula (1), having high luminescence efficiency and enhanced thermal-stability:

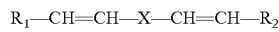

$R_1$—CH=CH—X—CH=CH—$R_2$ wherein, $R_1$, $R_2$ and X each are as defined below.

In addition, the present invention relates to an organic electroluminescent device containing the red color emitting compounds, particularly to an organic electroluminescent device having one or more organic thin layers comprising a luminescence region formed between a first electrode and a second electrode, wherein at least any one layer of the organic thin layers comprises one or more compounds represented by the above formula (1).

BACKGROUND OF THE INVENTION

The field of display device is very important for the information and communication industry. Recently in accordance with the development of information and communication technology, more advanced performance in this field has been asked for. Display can be divided into luminescent type and non-luminescent type. The luminescent type of display comprises Cathode Ray Tube (CRT), Electroluminescence Display (ELD), Light Emitting Diode (LED), Plasma Display Panel (PDP), etc. The non-luminescent type of display comprises Liquid Crystal Display (LCD), etc.

The luminescent and non-luminescent type of displays have such basic performances as operation voltage, consumption power, brightness, contrast, response rate, life time, etc. However, LCD, which has been widely used up to now, has some problems in the above basic performances in regard to response rate, contrast, and sight dependency. Thus, the LED-using display is anticipated to take the place of next-generation display device by solving the above LCD problems and by providing many other advantages such as fast response speed, no need for back light due to self-emission, and excellent brightness.

However, LED is mainly used with a crystal form of inorganic material, and so is hard to be applied to a large size of electroluminescent device. In addition, the electroluminescent device using inorganic material is very expensive and needs more than 200 V of operation voltage. However, Eastman Kodak reported in 1987 that the company manufactured a device made of a material having π-conjugate structure such as alumina quinine, and thereafter, the study for electroluminescent device using organic material has been more active.

The electroluminescence device (EL device, below) can be divided into inorganic EL device and organic EL device, depending on what material is used to form the emission layer (emitter layer).

The organic EL device, which is a self-emitting type of device that electrically excites fluorescent organic compound, is superior to the inorganic EL device in brightness, operation voltage, and response rate, and also can emit multi-colors.

In addition, the organic EL device is a luminescent device to emit in low voltage current, and has superior properties such as enhanced brightness, high speed of response, wide viewing angle, plane luminescence, slim type, and multi-color luminescence.

Thus, the organic EL device is expected to be applicable to a full-color plat panel display due to such superior properties that cannot be found in other displays.

C. W. Tang et al. reported the first practical device performance of the organic EL device in Applied Physics Letters, vol. 51 (12) pp 913-915 (1987). They developed a laminated-structure thin film (a hole transport layer) of formed by diamine analogues as organic layer and a thin film (an electron transport layer) formed by tris(8-quinolinolate) aluminum (Alq3, below). The laminated structure can lower the injection barrier of electron and hole from both electrodes to the organic layer, and also can enhance the re-combination probability of electron and hole from the inner organic layer.

Later, C. Adachi et al. developed an organic EL device having an organic luminescent layer with three-laminated structure of hole transport layer, emission layer, and electron transport layer [Japanese Journal of Applied Physics, vol. 27 (2), pp L269-L271 (1988)], and two-laminated structure of hole transportable emission layer and electron transport layer [Applied Physics Letter, vol. 55 (15), pp 1489-1491 (1989)], and showed that the optimization of device property can be achieved by constructing a multi-layer structure suitable for materials and combination thereof.

The organic EL comprises a first electrode (anode), a second electrode (cathode), and organic luminescent media. The organic luminescent media have at least two separate organic luminescent layers, i.e. one layer to inject and transport electron, and the other layer to inject and transport hole into the device. In addition, another multi-layer of thin organic film can be involved. The above layers to inject and transport electron and hole each can be divided into an electron injection layer, an electron transport layer, a hole injection layer, and a hole transport layer. In addition, the organic luminescent media can further include an emission layer besides the above layers.

The simple structure of organic EL device comprises a first electrode/an electron transport layer, and an emission layer/a second electrode. In addition, the structure of organic EL device can be separated into a first electrode/a hole injection layer/a hole transport layer/an emission layer/an electron transport layer/an electron injection layer/a second electrode.

The operation principle of the organic EL device having the above structure is as follows.

If the voltage is applied to the anode and cathode, the hole injected from the anode is transferred to the emission layer via the hole transport layer. Meanwhile, the electron is injected from the cathode to the emission layer via the electron transport layer. The hole and electron are re-combined in the emission layer to form exiton. The exiton is changed from the excitation state to the basic state, and thereby the fluorescent molecule of the emission layer becomes luminescent to form images.

The manufacturing process of a conventional organic EL device is explained with referring to FIG. 1 as follows.

First of all, an anode material 2 is formed on a transparent substrate such as glass 1. This time, Indium Tin Oxide (ITO: $In_2O_3+SnO_2$) is generally used as the anode material 2. On the anode material 2 may be formed either the hole injection layer (HIL) 3 or the hole transport layer (HTL) 4, or both HIL 3 and HTL 4 in order.

Here, Copper (II) Phthalocyanine (CuPC) of the thickness of 0 to 30 nm is generally used as HIL 3, and N,N-di(naphthalen-1-yl)-N,N'-diphenylbenzidine (NPD) of the thickness of about 30 to 60 nm as HTL 4.

Then, an organic emission layer 5 is formed on HIL 3 or HTL 4. Particularly, the luminescent material may be used alone as the emission layer 5, or used by doping a small quantity of impurity to the host material as occasion arises. For example, in case of green color emitting, tris(8-hydroxyquinolate) aluminum [Alq3] of the thickness of about 30 to 60 nm is usually used as host, and MQD (N-methylquinacridone) is usually used as dopant of the organic emission layer 5.

Next, an electron transport layer 6 or an electron injection layer 7 is independently or subsequently formed on the emission layer 5. Alq3 is usually used as the electron transport layer in the thickness of about 20 to 50 nm, and alkali metal analogue is used as the electron injection layer in the thickness of about 30 to 50 nm. In case of green color emitting, since Alq3 used as the organic emission layer has superior electron transport ability, the electron transport layer 6 or the electron injection layer 7 cannot be used.

Further, a second electrode (cathode) 8 is formed on the electron transport layer 6 or the electron injection layer 7, and a protecting layer is formed at the last.

Three luminescent devices emitting green, red and blue colors usually need to actualize full color of the organic EL device.

The blue color is actualized by doping a blue color emitting dopant onto a blue color emitting host and using Alq3 as the electron transport layer, and Alq3 may be omitted depending on the property of blue host. In case of red color emitting device, the red wavelength can be obtained by doping a red color emitting dopant, instead of a green color emitting dopant, during the above preparation of the device.

In case of green color emitting device, Coumarine 6 or Quinacridone analogue is used as dopant, and in case of red color emitting device, DCM (4-dicyanomethylene-6-(p-dimethylaminostylyl)-2-methyl-4H-pyrnae) analogue, such as DCM1 or DCM2, etc., is used as dopant [see, Journal of Applied Physics, 3610 (1989)].

However, in case of green color emitting device, the safety of the device is evaluated to have reached a practical level, but the red color emitting device has a problem that the luminescent color and the safety of the device have not reached such a level.

That is, among three luminescent devices of red/green/blue, the development of red color emitting device has been latest, and sufficient brightness and chromaticity therefor could not be obtained yet. For example, the peak wavelength of luminescent spectrum of the above DCM is about 600 nm, and the half band width is as broad as about 100 nm, therefore, the chromaticity as red corresponding to full-color is greatly lowered. In addition, if the concentration of red color emitting dopant such as DCM is small, the orange region spectrum is obtained, and if that concentration is rich, the red region is emitting but the luminescent efficiency is lowered by self quenching. Further, the red color emitting device using Alq3 [tris(8-hydroxy quinolate)aluminum] doped by DCJTB [4-(Dicyanomethylene)-2-tert-butyl-6-(tetramethyljulolidi-4-yl)-4H-pyran] as electron transport material is not satisfactory as display material in view of lightness and chromaticity thereof.

However, the organic metal complexes, whose central metal is europium, have been known as the red color emitting device having high chromaticity, but the maximum lightness of the organic EL device using them is very low [see, Applied Physics Letter, 65 (17), 2124~2126 (1994)].

In addition, Japanese Patent Publication No. 1999-329731 has been disclosed to manufacture the red color emitting organic EL device having high brightness by using specific di-styryl compounds, but the half band width of luminescent spectrum is more than 100 nm, and thus the chromaticity thereof cannot be said complete.

To solve the above problems, the present inventors have conducted intensive studies to develop a red color emitting material that is safe at high brightness and has good chromaticity, and completed the present invention.

SUMMARY OF THE INVENTION

An object of the present invention is to provide a novel red color emitting material having high luminescence efficiency and enhanced thermal-stability to manufacture a stable red color emitting organic EL device having high red chromaticity and high brightness.

Another object of the present invention is to provide an organic electroluminescent device comprising the above material which has high brightness and high luminescence efficiency by facilitating the recombination of hole and electron in an emission layer.

In order to accomplish these objects of the present invention, the present invention provides red color emitting compounds for an organic EL device represented by the following formula (1):

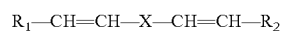

wherein,

X is

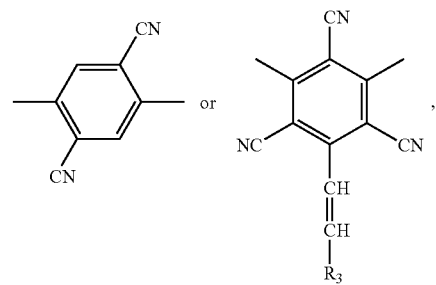

$R_1$, $R_2$ and $R_3$ each are independently formula (2), formula (3), formula (4) or formula (5),

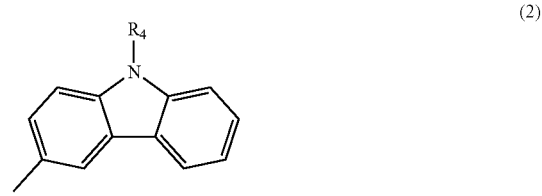

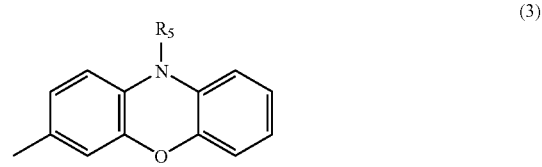

-continued

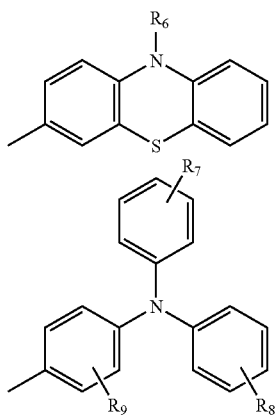

wherein,
$R_4$, $R_5$, $R_6$, $R_7$, $R_8$ and $R_9$ each are independently a hydrogen atom, a halogen group, a substituted or unsubstituted alkoxy group, a substituted or unsubstituted alkyl group, or a substituted or unsubstituted allyl group.

Preferred Embodiments of the Invention

Each definition in the above formula will be shown in detail hereinbelow.

According to the present invention, a preferable example of the "alkyl group" is a straight or branched chain saturated hydrocarbon group having 1 to 5 carbon atoms, for example, methyl, ethyl, propyl, isopropyl, butyl, isobutyl, t-butyl, pentyl, isopentyl, etc., but more preferably, the ethyl group can be used.

A preferable example of the "alkoxy group" is a group containing a straight or branched alkyl having 1 to 5 carbon atoms, for example, methoxy, ethoxy, propoxy, isopropoxy, butoxy, isobutoxy, t-butoxy, pentoxy, isopentoxy, etc., but more preferably, the ethoxy group can be used.

A preferable example of the "allyl group" is an aromatic group having 6 to 12 carbon atoms, for example, phenyl, naphthyl, etc., but more preferably, the naphthyl group can be used.

According to the present invention, a preferable example of the "substituents" is hydrogen atom, halogen group, cyano group, amino group, nitro group, carboxy group, methyl group, ethyl group, propyl group, butyl group, sec-butyl group, tert-butyl group, pentyl group, hexyl group, etc., but is not limited thereto.

The representative examples of formula (1) are described below.

Compound 1

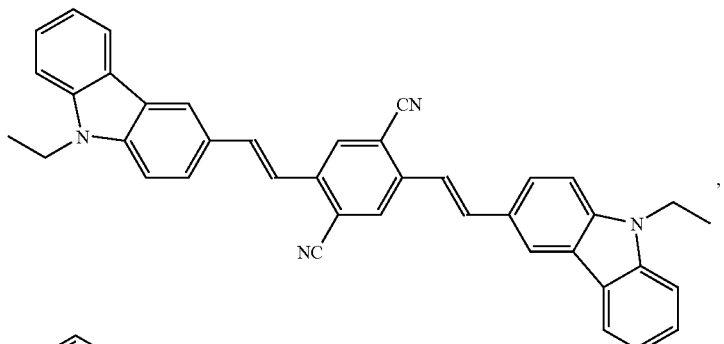

Compound 2

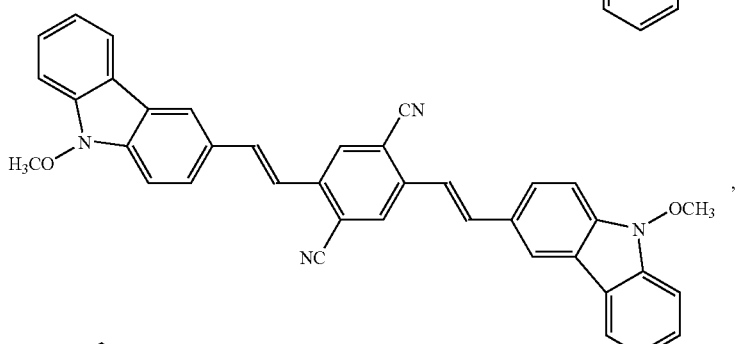

Compound 3

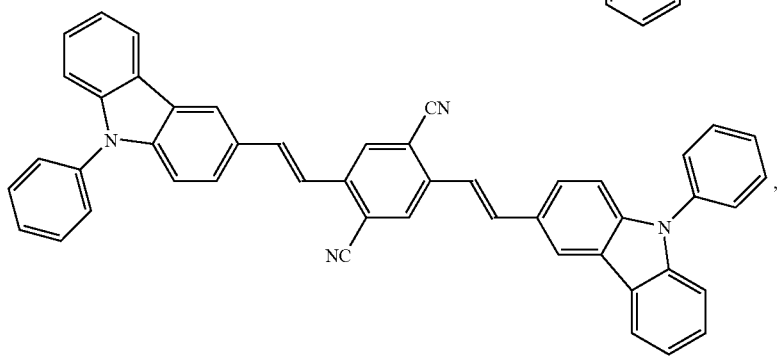

-continued
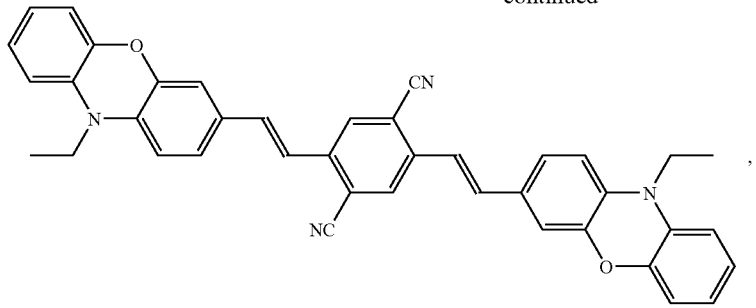
Compound 4
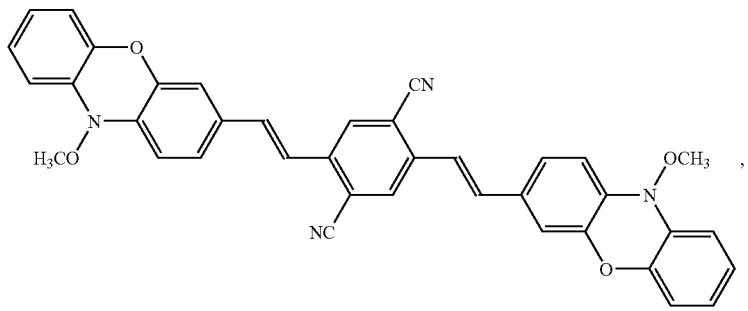
Compound 5
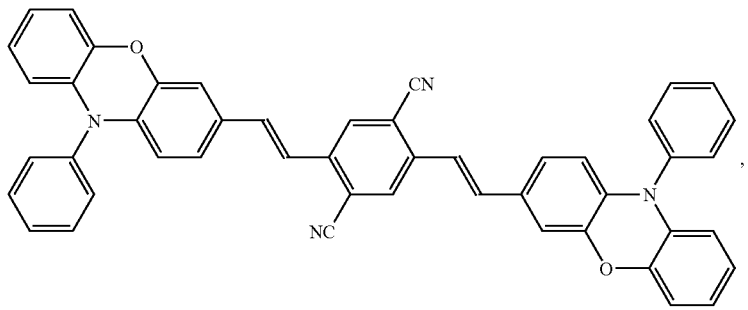
Compound 6
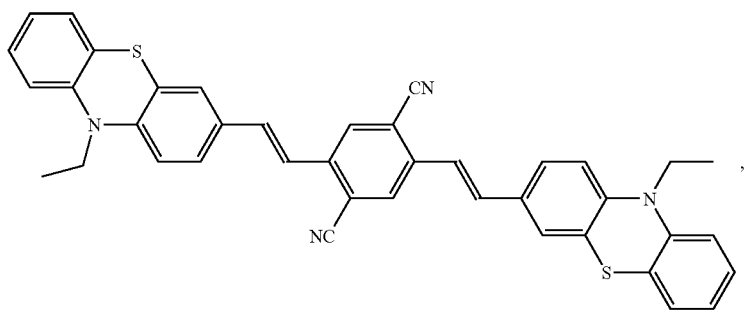
Compound 7
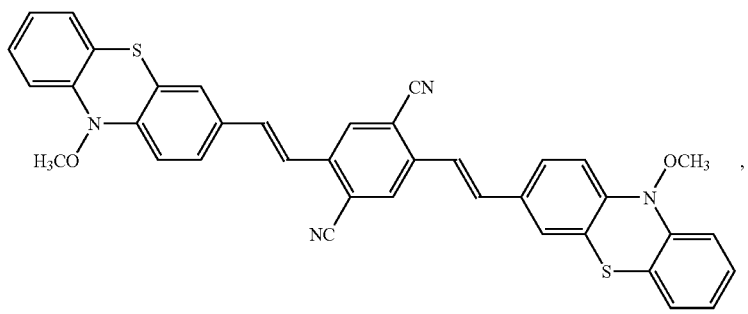
Compound 8

-continued
Compound 9
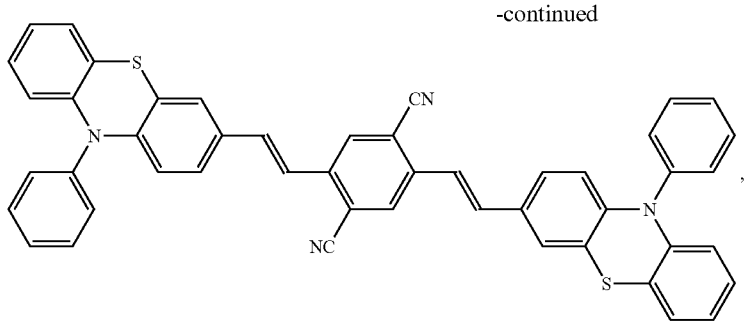
Compound 10
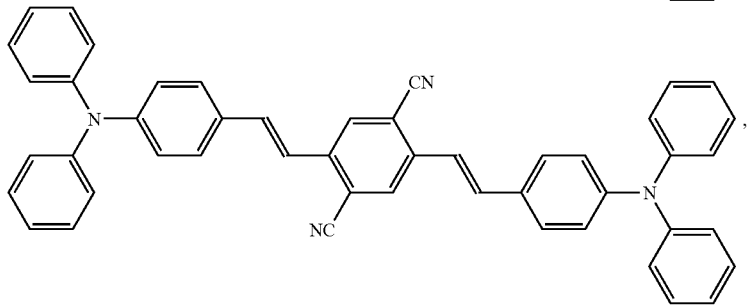
Compound 11
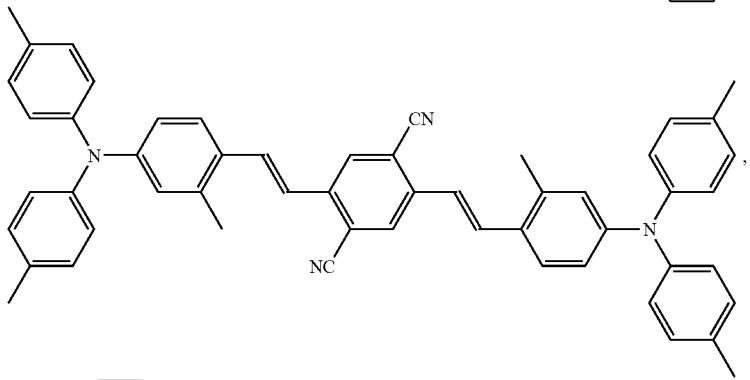
Compound 12
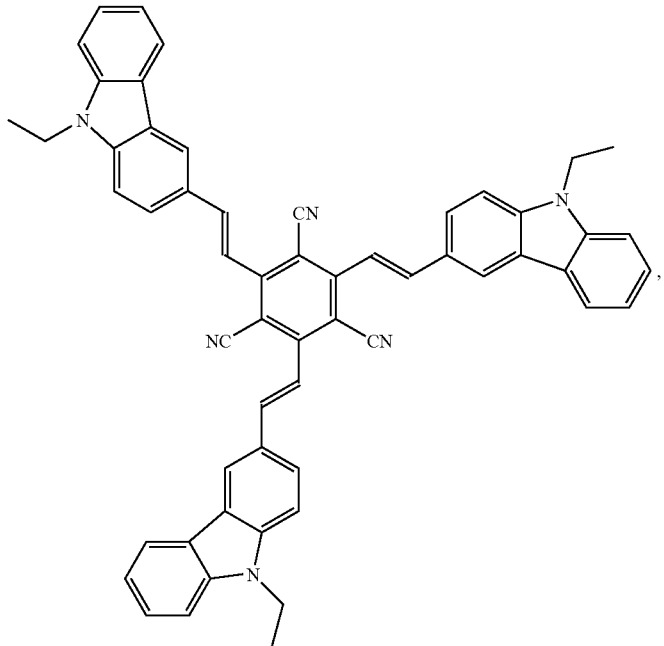

-continued
Compound 13
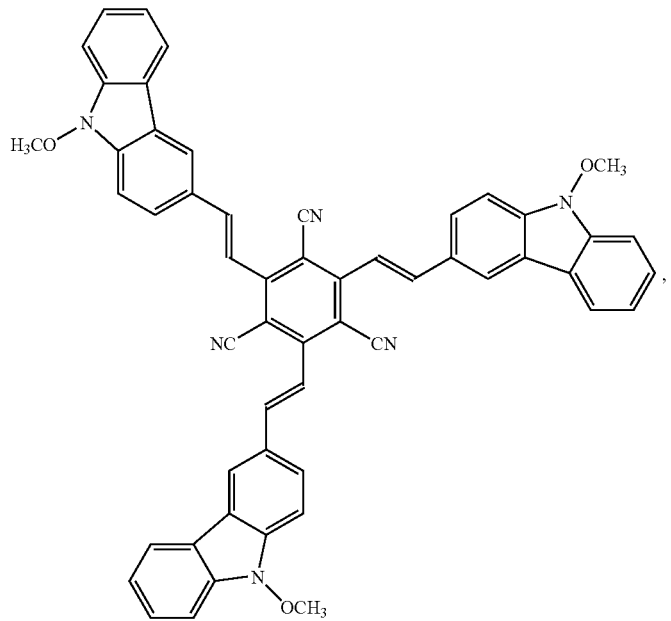
Compound 14
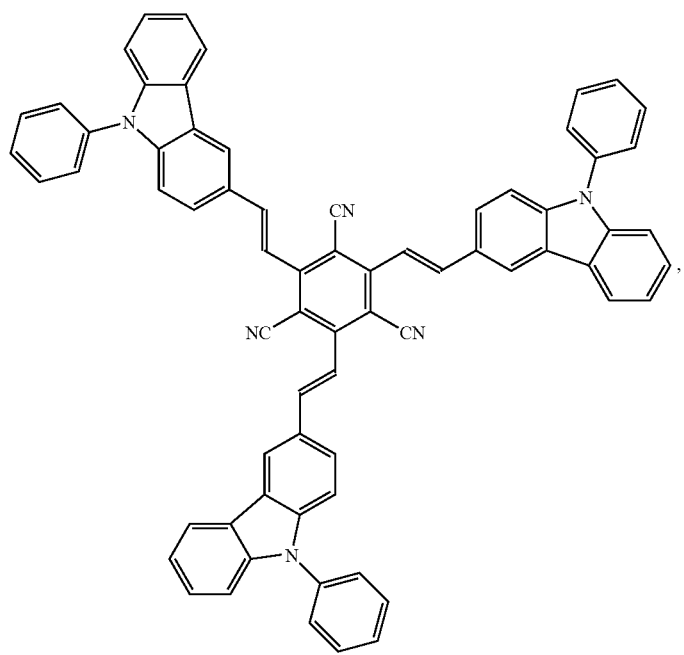

Compound 15
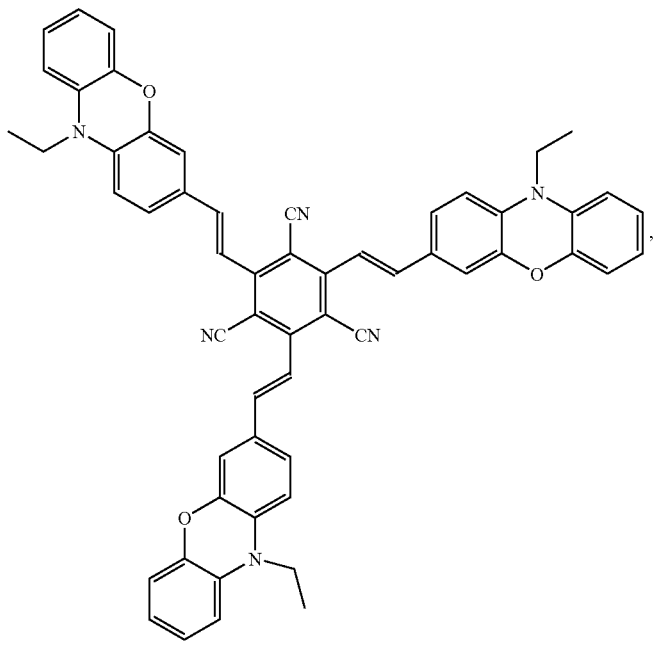
Compound 16
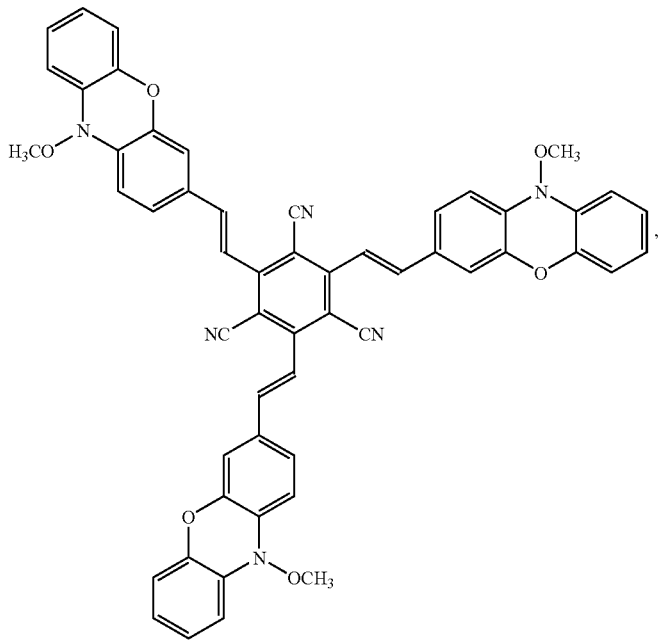

Compound 17
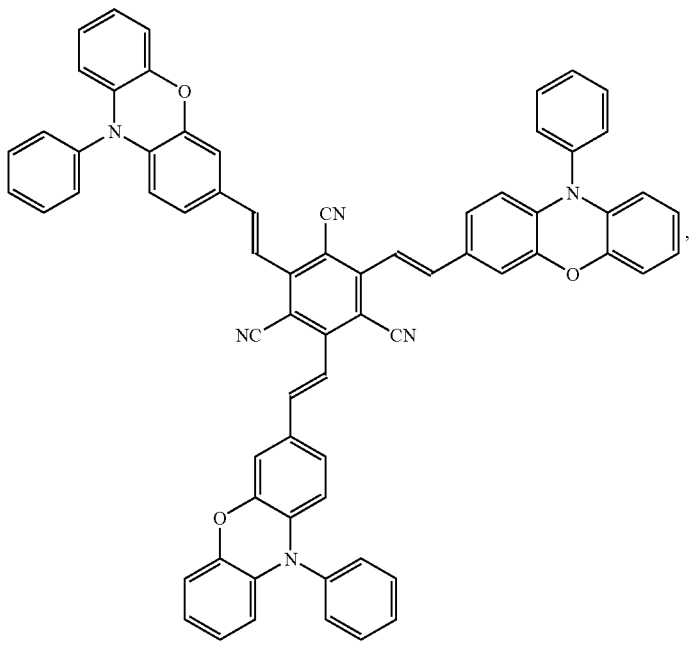
Compound 18
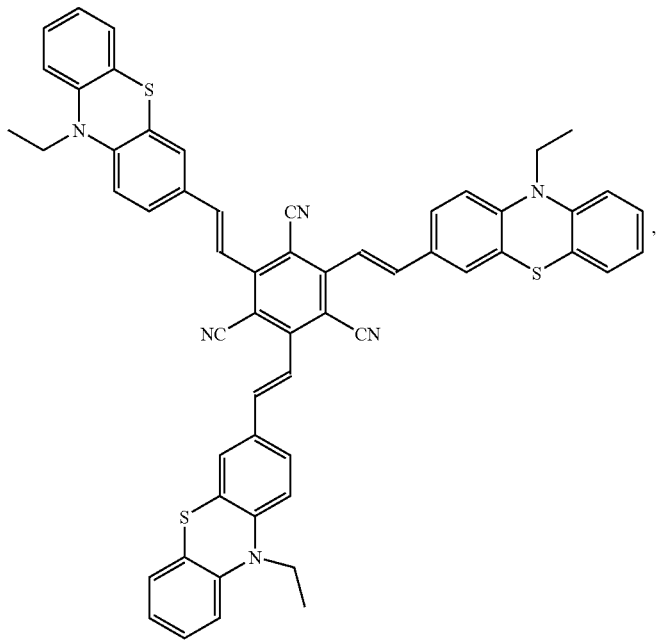

-continued
Compound 19
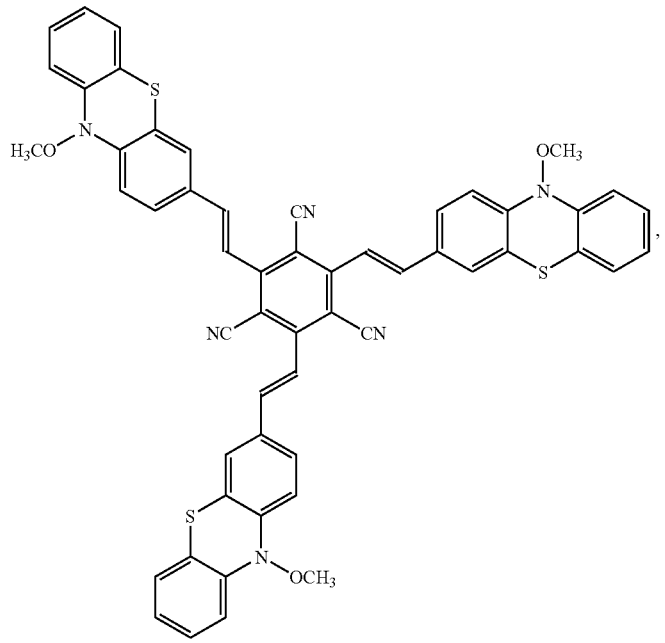
Compound 20
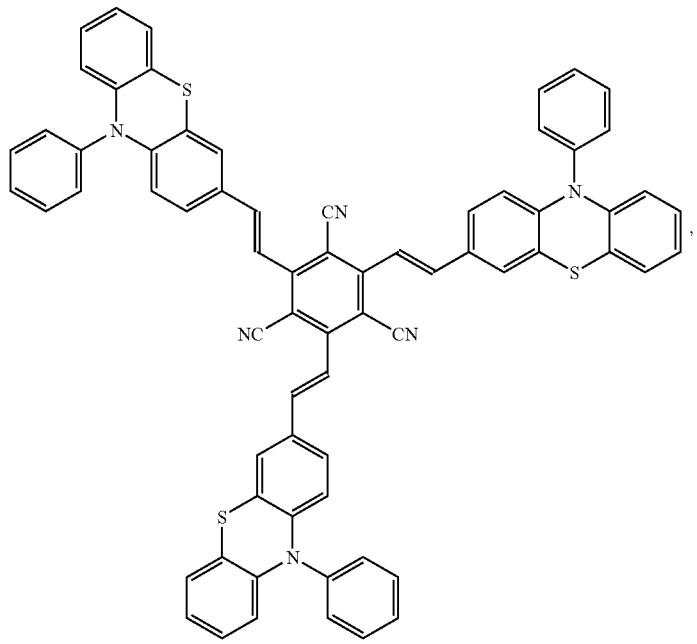

Compound 21

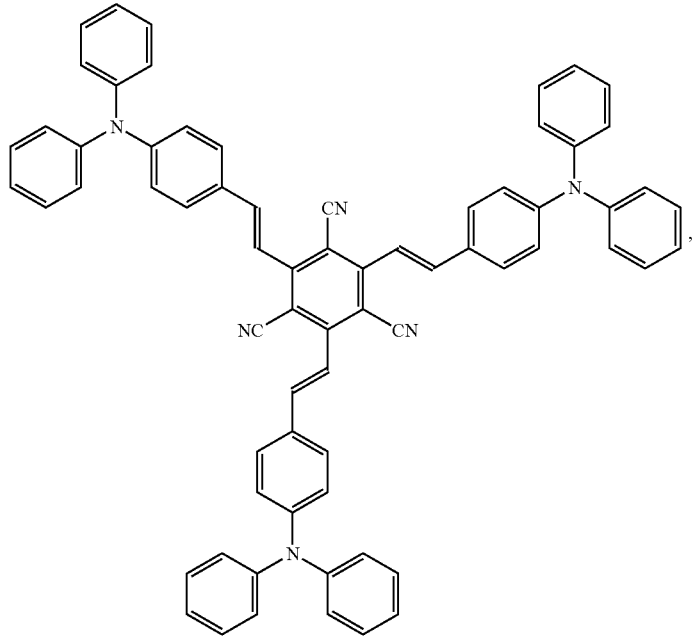

Compound 22

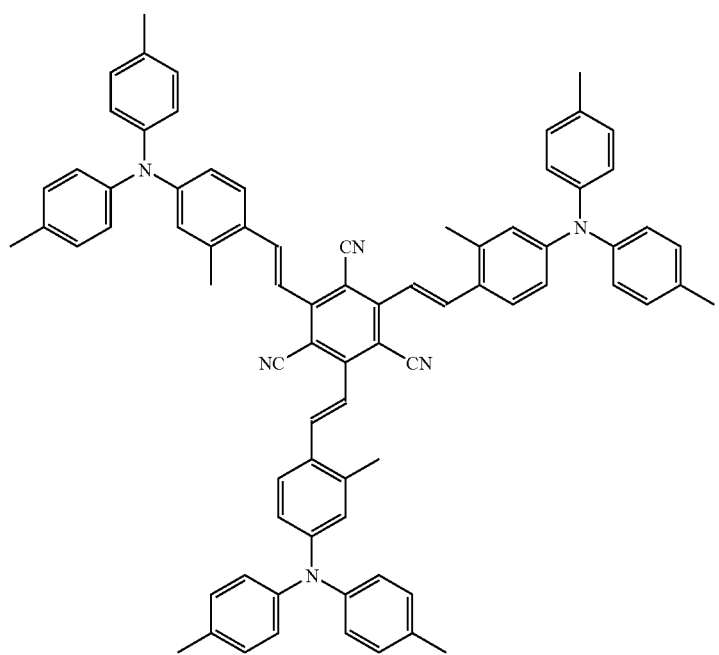

However, the present invention shall not be limited by these representative examples.

In addition, the present invention provides an organic EL device comprising the compound of formula (1), more specifically, an organic EL device having one or more organic thin layers formed between the first electrode and the second electrode, wherein at least any one layer of the organic thin layers comprises one or more red color emitting materials according to the present invention.

The compound of formula (1) can be used alone, in a type of combination, or as host doped by other materials, to any of the organic thin layers, or used as dopant to the other hole transport material, emission material, or electron transport material. Preferably, the compound of the present invention can be used as dopant or host to the emission layer.

A variety of embodiments of the organic EL device using the red color emitting materials of the present invention can be achieved. Basically, the emission layer, if necessary, is introduced into the pair of electrodes (anode and cathode). Then, if necessary, a hole injection layer and/or a hole transport layer and/or an electron injection layer and/or an electron transport layer can be introduced. More specifically, the structure examples of the device are: (1) anode/emission layer/cathode; (2) anode/hole transport layer/emission layer/ cathode; (3) anode/hole transport layer/electron transport layer/cathode; (4) anode/hole injection layer/hole transport layer/emission layer/cathode; (5) anode/hole injection layer/ hole transport layer/emission layer/electron transport layer/ cathode; (6) anode/hole injection layer/hole transport layer/ emission layer/electron transport layer/electron injection layer/cathode; and (7) anode/hole injection layer/emission layer/electron injection layer/cathode, etc. If necessary, the device having the above structures is supported by a substrate. No particular limitation exists for the substrate, and the conventional substrate used in the organic EL device, such as glass, transparent plastics, quartz, etc., can be used.

Each layer constructing the organic EL device of the present invention can be formed by applying the comprising materials under the conventional methods such as deposition method, spin-coat method, or cast method, to laminate the layers.

No particular limitation exists on the thickness of each layer, such as emission layer, formed by such method, and a suitable selection may be made depending on conditions of the device.

In addition, for the anode of the organic EL device, a metal having work function more than 4.0 eV, alloy, electric-conductive compound, or combination thereof, can be used as electrode. The examples of such electrode material are electric conductive transparent or non-transparent materials, such as ITO, $SnO_2$, ZnO, Au, etc. The anode can be manufactured by forming a thin film through the method of deposition, sputtering, etc.

Besides, for the cathode of the organic EL device, a metal having work function less than 4.2 eV, alloy, electric-conductive compound, or combination thereof, can be used as electrode. The examples of such electrode material are calcium, magnesium, lithium, aluminum, magnesium alloy, lithium alloy, aluminum alloy, aluminum/lithium mixture, magnesium/silver mixture, indium, etc. The cathode also can be manufactured by forming a thin film through the method of deposition, sputtering, etc.

Preferably, the sheet resistance as electrode is less than several hundreds Ω/mm, and the thickness of film is selected in the range of 10 nm to 1 μm, preferably 50 to 200 nm.

For the organic EL device of the present invention, it is preferable to make each or both of anode and cathode transparent or semi-transparent, and transmit the luminescence through the anode or cathode to enhance the transmission effect of the luminescence.

For other materials for hole injection layer and hole transport layer in the organic EL device of the present invention can be used any material conventionally used as hole transport material among photo-conductive materials, and any random material among known materials used as hole injection layer or hole transport layer.

For the organic EL device of the present invention, an electron transport layer comprises an electron transport compound, and has a role to transport electron injected from the cathode to the emission layer. No particular limitation exists for such electron transport compound, and any known conventional compound can be selected thereat.

Below, one embodiment of suitable methods to manufacture the organic EL device of the present invention having the above six (6) structures is explained as follows:

First of all, a first electrode is formed on a transparent substrate, for example, by using sputtering method. Then, a hole transport layer and a hole transport layer are formed thereon in order by deposition in vacuum. After that, an organic emission layer and an electron transport layer are subsequently formed on the hole transport layer, and the electron injection layer and a cathode are subsequently formed on the electron transport layer.

The emission layer can be formed by a conventional host doped with one or more dopants of formula (1) of the present invention, or only by one or more compounds of formula (1) of the present invention. In addition, the compound of formula (1) of the present invention can be formed as the emission layer by using each other as host and dopant.

ITO ($In_2O_3$+$SnO_2$) or IZO ($In_2O_3$+ZnO) can be usually used for the material of the anode, and copper (II) phthalocyanine can be used for the material of the hole injection layer. Triphenylamine or diphenyl amine analogues such as NPD (N,N-di(naphthalen-1-yl)-N,N'-diphenylbenzidine) can be used for the material of the hole transport layer, and Alq3 (tris(8-hydroxyquinolate)aluminum) can be used for the host material of the emission layer. In addition, Alq3 can be also used for the electron transport layer due to good electron transport property, oxadiazole or triazole analogues such as 2-(4-bi-phenyl)-5-(4-tert-butylphenyl)-1,3,4-oxadiazole can be also used for the electron transport layer. Alkali metal (Cs, Rb, K, Na, Li) analogues ($Li_2O$; etc.) can be used for the electron injection layer, and Mg/Ag, Al, Al/Li, or Al/Nd can be used for the cathode.

BRIEF DESCRIPTION OF THE DRAWINGS

The present invention will be more clearly understood from the detailed description in conjunction with the following drawings.

FIG. 1 is a schematic sectional view of the conventional organic EL device.

DETAILED DESCRIPTION OF THE INVENTION

The synthetic examples of the compounds of formula (1) of the present invention, and the organic EL device applied with the compounds are explained through the synthetic examples and practicing examples below. Additional advantages, objects, and features of the present invention will be set forth in the description which follows and will also become apparent to those who practice the present invention. The objectives and other advantages of the present invention will be explained in the written description including the claims.

SYNTHETIC EXAMPLES

Synthetic Example 1

Synthesis of 2,5-bis-[2-(9-ethyl-carbazol-3-yl)-vinyl]-terephthalonitrile (Compound 1)

1) Synthesis of 2,5-dimethyl-terephthalonitrile 60 g of 2,5-Dibromo-p-xylene (0.227 mole), 42.4 g of CuCN (0.568 mole) and 300 ml of dimethylformamide were added into a round-bottom flask, and then the reaction was performed at 130° C. for 12 hours. After completion of the reaction, the reaction mixture was added to the mixing solution of 300 ml of water and 300 ml of aqueous ammonia, and extracted crystal therefrom was filtered. Then, the crystal was added again to the mixing solution of 100 ml of water and 300 ml of aqueous ammonia, mixed and filtered. The obtained crystal was added to 2,000 ml of toluene, heated to dissolve, and treated with active carbon. The filtrate was evaporated in vacuum, and then 300 ml of hexane was added thereto to obtain 20 g of white crystal (0.128 mole, yield: 56%).

2) Synthesis of 2,5-dibromomethyl-terephthalonitrile 2 g of 2,5-dimethyl-terephthalonitrile (0.0128 mole), 1.9 ml of bromine (0.384 mole) and 100 ml of dichloromethane were added to a middle pressure tube, and the reaction was performed at 60° C. for 24 hours. After completion of the reaction, 200 ml of water was added thereto, and then the pH of the reaction solution was pH 10 with 2% sodium hydroxide. After the organic layer was separated, extracted by 200 ml of water two times, and evaporated in vacuum. The concentrated crystal was loaded to column with hexane to obtain 1.1 g of product (3.5 mole, yield: 27.5%).

3) Synthesis of [2,5-dicyano-4-(diethoxy-phosphorylmethyl)-benzyl]-phosphonic acid diethyl ester 3 g of 2,5-dibromomethyl-terephthalonitrile (9.55 mmole), 6.6 ml of triethoxyphosphate (0.038 mole) and 100 ml of toluene were added into a round-bottom flask, and refluxed for 24 hours. After completion of the reaction, the reaction mixture was treated with active carbon, and the filtrate was evaporated in vacuum to obtain 3 g of white crystal (7.0 mmole, yield: 75%).

4) Synthesis of 2,5-bis-[2-(9-ethylcarbazol-3-yl)-vinyl]-terephthalonitrile 1.3 g of [2,5-dicyano-4-(diethoxy-phosphorylmethyl)-benzyl]-phosphonic acid diethyl ester (3.03 mmole), 1.4 g of 9-ethyl-carbazolaldehyde, and 100 ml of tetrahydrofuran were added into a round-bottom flask. 0.7 g of t-butyloxide potassium (6.37 mmole) divided by several times was slowly added to the reaction mixture, and then the resulting mixture was stirred at ambient temperature for 1 hour, 200 ml of water was added thereto, and then the produced crystal was filtered and washed with 50 ml of methyl alcohol. The obtained crystal was added to 100 ml of dichloromethane, mixed, and filtered to obtain 0.8 g of orange crystal (1.41 mmole, yield: 46%). The melting point of the final compound was measured to 333° C.

Synthetic Example 2

Synthesis of 2,5-bis-[2-(10-ethyl-phenocyazin-3-yl)-vinyl]-terephthalonitrile (Compound 4)

1.3 g of [2,5-dicyano-4-(diethoxy-phosphorylmethyl)-benzyl]-phophosphonic acid diethyl ester (3.03 mmole), 1.54 g of 10-ethyl-3-phenocyazine aldehyde (6.06 mmole), and 100 ml of tetrahydrofuran were added into a round-bottom flask. 0.7 g of t-butyloxide potassium (6.37 mmole) divided by several times was slowly added to the reaction mixture, and then the reaction mixture was stirred at ambient temperature for 1 hour. Then, 200 ml of water wad added thereto, and the produced crystal was filtered, and washed with 50 ml of methyl alcohol. 100 ml of dichloromethane was added to the obtained crystal, stirred and filtered to obtain 0.94 g of orange crystal (yield: 49%).

Synthetic Example 3

Synthesis of 2,5-bis-[2-(10-ethyl-phenoxazin-3-yl)-vinyl]-terephthalonitrile (Compound 7)

1.3 g of [2,5-dicyano-4-(diethoxy-phosphorylmethyl)-benzyl]-phophosphonic acid diethyl ester (3.03 mmole), 1.45 g of 10-ethyl-3-phenocyazine aldehyde (6.06 mmole), and 100 ml of tetrahydrofuran were added into a round-bottom flask. 0.7 g of t-butyloxide potassium (6.37 mmole) divided by several times was slowly added to the reaction mixture, and then the reaction mixture was stirred at ambient temperature for 1 hour. Then, the produced crystal was filtered, and washed with 50 ml of methyl alcohol. 100 ml of dichloromethane was added to the obtained crystal, stirred and filtered to obtain 0.72 g of orange crystal (yield: 39%).

Synthetic Example 4

Synthesis of 2,5-bis-[4-(triphenylamine)-vinyl]-terephthalonitrile (Compound 10)

1.3 g of [2,5-dicyano-4-(diethoxy-phosphorylmethyl)-benzyl]-phophosphonic acid diethyl ester (3.03 mmole), 1.65 g of 4-formyltriphenyl aldehyde (6.06 mmole), and 100 ml of tetrahydrofuran were added into a round-bottom flask. 0.7 g of t-butyloxide potassium (6.37 mmole) divided by several times was slowly added to the reaction mixture, and then the reaction mixture was refluxed and cooled to obtain a crystal. Then, the produced crystal was filtered, and washed with 200 ml of methyl alcohol. 100 ml of dichloromethane was added to the obtained crystal, stirred and filtered to obtain 0.8 g of orange crystal (1.41 mmole, yield: 39%).

Synthetic Example 5

Synthesis of Compound 22

1) Synthesis of 2,4,6-tribromo-1,3,5-trimethylbenzene

A brome crude liquid (14 ml, 0.27 mmol), iron powder (4 g, 72 mmol), and carbon tetrachloride (30 ml) were added to a reaction vessel, and then 1,3,5-trimethylbenzene (2 ml, 14 mmol) was slowly added thereto over 1 hour. The reaction mixture was further stirred for 1 hour, and then $Na_2S_2O_3$ solution was excessively added thereto and brome was excluded. Then, this solution was extracted with water/chloroform to eliminate solvent thereof, and re-crystallized with the mixing solution (toluene/acetone=1/5) to obtain white product [yield: 3.5 g (70% over)].

2) Synthesis of 2,4,6-tricyano-1,3,5-trimethylbenzene (TCM)

CuCN (220 g, 243 mmol) and pyridine (146.7 g, 1.85 mol) were added to a high pressure reaction vessel, and well mixed, and then 2,4,6-tribromo-1,3,5-trimethylbenzene(25 g, 75.8 mmol) was added thereto. The reaction mixture was reacted at 205° C. for 2 hours. Cu therein was excluded with excessive methylene diamine, and then filtered by MC. Water in the reaction mixture was eliminated over $MgSO_4$, and then solvent therein was evaporated in vacuum. The residue was absorbed to silica gel column and separated with a tube chromatography (Hx:MC=3:1) to obtain white solid [yield : 6 g (40.59%)].

3) Synthesis of 2,4,6-tricyano-bromomethylbenzene-1,3,5-tricarbonitrile (TCBM)

TCM (1 g, 5.128 mmol), bromine (2.86 g, 17.248 mmol), and carbon tetrachloride (10 ml) were added to a light reactor, and then reacted by tungsten lamp for 8 hours. The reaction mixture was extracted by MC, and water therein was excluded over $MgSO_4$, and then the solvent was evaporated in vacuum. The residue was separated with a tube chromatography (Hx:EA=8:1) to obtain white solid [yield: 1.32 g(60%)].

4) Synthesis of (2,4,6-tricyano-3,5-bis[diethoxy-phosphoryl]-phenyl)-phosphonic acid diethyl ester (TCPM)

TCBM (1 g, 2.32 mmol), triethylphosphite (1.616 g, 13.92 mmol), and toluene (excess amount) were added to a reaction vessel, and refluxed for 8 hours. After the solvent was evaporated in vacuum and excluded, the residue was separated with a tube chromatography (Hx:MC=3:1) to obtain yellow liquid [yield: 0.84 g (60%)].

5) Synthesis of m-toryl-di-p-torylamine (MTPA)

A high pressure tube, dried by a dry oven, was filled with argon gas, and then m-toryl amine (1 g, 9 mmol), 1-bromo-4-methyl-benzene (6.2 g, 36 mmol), pd(dba)$_3$ (0.39 g, 0.43 mmol), DPPF (0.48, 0.86 mmol), NaOtBu (4.1 g, 43 mmol), and toluene (20 ml) were added thereto, and stirred at 120°

C. for 72 hours. The reaction mixture was extracted by MC, and the solvent was evaporated in vacuum. The residue was filtered with a tube chromatography (Hx:EA=10:1), and re-crystallized with hexane to obtain white solid [yield: 1.07 g (40%)].

6) Synthesis of TPAD

After MTPA (0.2 g, 0.69 mmol) was dissolved into DMF (20 ml), POCl$_3$ (0.15 g, 1 mmol) was added thereto dropwise at 0° C. The reaction mixture was stirred over 30 minutes, and then the temperature thereof was elevated to 90° C. to react for 4 hours. The reaction mixture was added to 50 ml of iced water, and neutralized with 20% NaOH solution, and extracted by MC. After the solvent was evaporated in vacuum and eliminated, the residue was separated a tube chromatography (Hx:EA=15:1). [yield: 0.16 g (80%)]

7) Synthesis of Compound 22

LDA (0.84 ml, 0.51 mmol) was added to TCPM (0.1 g, 0.17 mmol) in 10 ml of THF at −72° C. condition, and after 30 minutes the bath was eliminated, and the reaction mixture was further stirred for 30 minutes. Then, the temperature thereof was lowered, TPAD (0.16 g, 0.51 mmol) was added thereto dropwise, stirred, and after 30 minutes the bath was eliminated for 30 minutes and allowed to overnight. The residue was separated with a tube chromatography (Hx:EA=1:4). [M.P.: 280° C., yield: 0.070 g (38%)].

Other compounds including formula (1) are synthesized by a similar method to Synthetic Examples 1 to 5. The synthesized materials as above were further purified with a vacuum sublimation apparatus to use in the organic EL device.

Example 1

For the present example, the organic EL device using compound 10 as dopant and Alq3 as host of a red color emitting layer was manufactured.

First, a hole injection layer was formed with the thickness of 30 nm by depositing CuPC (copper (II) phthalocyanine) in vacuum on an ITO-deposited glass washed by a microwave. Then, after a hole transport layer was formed with the thickness of 50 nm by depositing NPD (N,N'-dinaphthyl-N, N'-phenyl-(1,1'-biphenyl)-4,4'-diamine) in vacuum thereon, an emission layer is formed with the thickness of 30 nm on the hole transport layer by depositing Alq3 (host), which was doped with compound 10 (dopant) by 1.0%. An electron transport layer (Alq3; 40 nm), an electron injection layer (Li$_2$O; 25 nm), and a cathode (Mg/Ag; 100 nm) were formed in order thereon by depositing in vacuum to complete the organic EL device.

The direct voltage of forward bias was applied to the organic EL device manufactured by Example 1, and luminescent property thereof was evaluated. The luminescent color was red. As a result of spectroscopy, a spectrum having approximately 605 nm of luminescent peak was obtained. In addition, as a result of voltage-brightness test, 5,400 cd/m$^2$ of brightness at 8 V was obtained, at which point the efficiency was 1.88 lm/W (see Table 1).

Example 2

For the present example, the organic EL device using compound 1 as host and DCM as dopant of a red color emitting layer was manufactured.

First, a hole injection layer was formed with the thickness of 30 nm by depositing CuPC in vacuum on an ITO-deposited glass washed by a microwave. Then, after a hole transport layer was formed with the thickness of 50 nm by depositing NPD (N,N'-dinaphthyl-N,N'-phenyl-(1,1'-biphenyl)-4,4'-diamine) in vacuum thereon, an emission layer is formed with the thickness of 30 nm on the hole transport layer by depositing compound 1 (host), which was doped with DCM (dopant) by 1.0%. An electron transport layer (Alq3; 40 nm), an electron injection layer (Li$_2$O; 25 nm), and a cathode (Mg/Ag; 100 nm) were formed in order thereon by depositing in vacuum to complete the organic EL device.

The direct voltage of forward bias was applied to the organic EL device manufactured by Example 1, and luminescent property thereof was evaluated. The luminescent color was red. As a result of spectroscopy, a spectrum having approximately 609 nm of luminescent peak was obtained. In addition, as a result of voltage-brightness test, 5,740 cd/m$^2$ of brightness at 8.7 V was obtained, at which point the efficiency was 1.92 m/W (see Table 1).

Example 3

For the present example, the organic EL device using compound 22 as host and DCM as dopant of a red color emitting layer was manufactured.

First, a hole injection layer was formed with the thickness of 30 nm by depositing CuPC in vacuum on an ITO-deposited glass washed by a microwave. Then, after a hole transport layer was formed with the thickness of 50 nm by depositing NPD (N,N'-dinaphthyl-N,N'-phenyl-(1,1'-biphenyl)-4,4'-diamine) in vacuum thereon, an emission layer is formed with the thickness of 30 nm on the hole transport layer by depositing compound 22 (host), which was doped with DCM (dopant) by 1.0%. An electron transport layer (Alq3; 40 nm), an electron injection layer (Li$_2$O; 25 nm), and a cathode (Mg/Ag; 100 nm) were formed in order thereon by depositing in vacuum to complete the organic EL device.

The direct voltage of forward bias was applied to the organic EL device manufactured by Example 1, and luminescent property thereof was evaluated. The luminescent color was red. As a result of spectroscopy, a spectrum having approximately 621 nm of luminescent-peak was obtained. In addition, as a result of voltage-brightness test, 3,872 cd/m$^2$ of brightness at 8.5 V was obtained, at which point the efficiency was 1.48 m/W (see Table 1).

Example 4

For the present example, the organic EL device using compound 1 as host and compound 22 as dopant of a red color emitting layer was manufactured.

First, a hole injection layer was formed with the thickness of 30 nm by depositing CUPC in vacuum on an ITO-deposited glass washed by a microwave. Then, after a hole transport layer was formed with the thickness of 50 nm by depositing NPD (N,N'-dinaphthyl-N,N'-phenyl-(1,1'-biphenyl)-4,4'-diamine) in vacuum thereon, an emission layer is formed with the thickness of 30 nm on the hole transport layer by depositing compound 1 (host), which was doped with DCM (dopant) by 1.0%. An electron transport layer (Alq3; 40 nm), an electron injection layer (Li$_2$O; 25 nm), and a cathode (Mg/Ag; 100 nm) were formed in order thereon by depositing in vacuum to complete the organic EL device.

The direct voltage of forward bias was applied to the organic EL device manufactured by Example 1, and luminescent property thereof was evaluated. The luminescent color was red. As a result of spectroscopy, a spectrum having approximately 617 nm of luminescent peak was obtained. In addition, as a result of voltage-brightness test, 4,200 cd/m$^2$ of brightness at 7.8 V was obtained, at which point the efficiency was 1.55 m/W (see Table 1).

The results of the examples are summarized in Table 1 below.

TABLE 1

| | Host | Dopant | Applied Voltage (V) | Brightness (cd/m$^2$) | Efficiency (lm/W) | Spectrum (nm) |
|---|---|---|---|---|---|---|
| Example 1 | Alq3 | Compound 10 | 8.0 | 5,400 | 1.88 | 605 nm |
| Example 2 | Compound 1 | DCM | 8.7 | 5,740 | 1.92 | 609 nm |
| Example 3 | Compound 22 | DCM | 8.5 | 3,872 | 1.48 | 621 nm |
| Example 4 | Compound 1 | Compound 22 | 7.8 | 4,200 | 1.55 | 617 nm |

As shown in the above Table, the organic EL devices applied with the red color emitting materials of the present invention shows high advanced luminescent efficiency and brightness than the organic EL device applied with conventional red color emitting materials. In addition, the present materials contribute to enhance the safety and the life time of the device.

What is claimed is:

1. A compound represented by the following formula (1):

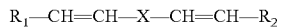

wherein,

X is

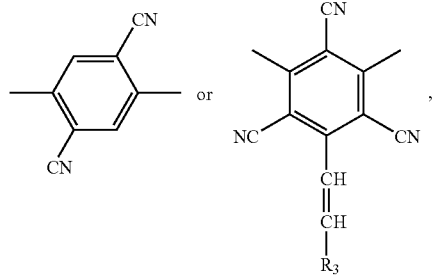

$R_1$, $R_2$ and $R_3$ each are independently formula (2), formula (3), or formula (4) or formula (5), with the proviso that $R_1$ and $R_2$ each are not formula (5) when x is 1,4-dicyanophenyl, and at least one of $R_1$, $R_2$ and $R_3$ are not formula (5) when X is 1,3,5-tricyanophenyl,

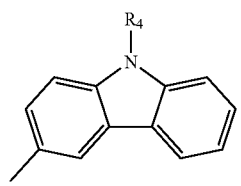
(2)

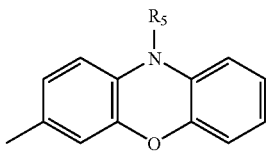
(3)

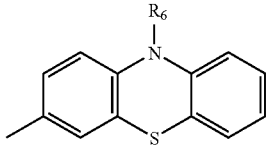
(4)

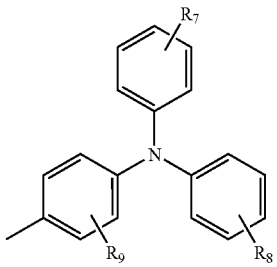
(5)

wherein, $R_4$, $R_5$, $R_6$, $R_7$, $R_8$ and $R_9$ each are independently a hydrogen atom, a halogen group, a substituted or unsubstituted alkoxy group, a substituted or unsubstituted alkyl group, or a substituted or unsubstituted allyl group.

2. The compound according to claim 1, wherein the compound is selected from the group consisting of:

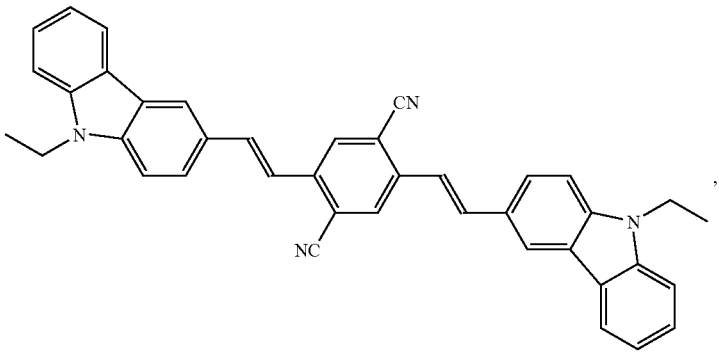

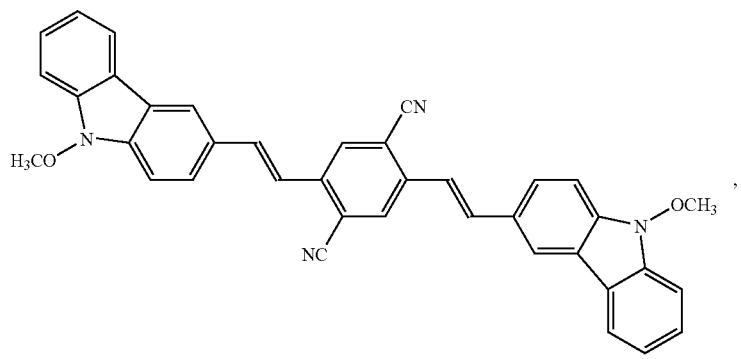
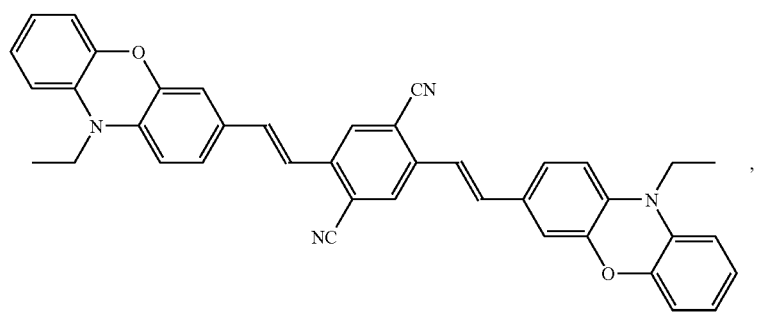
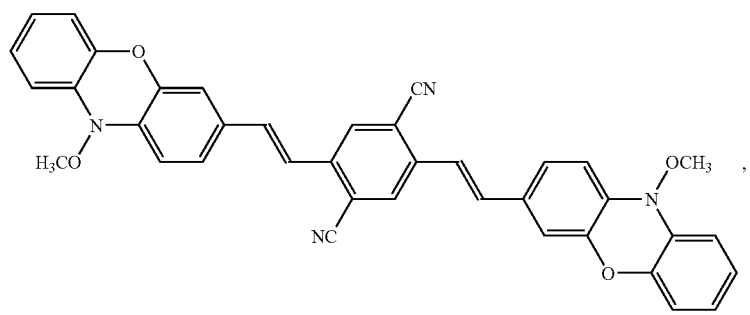
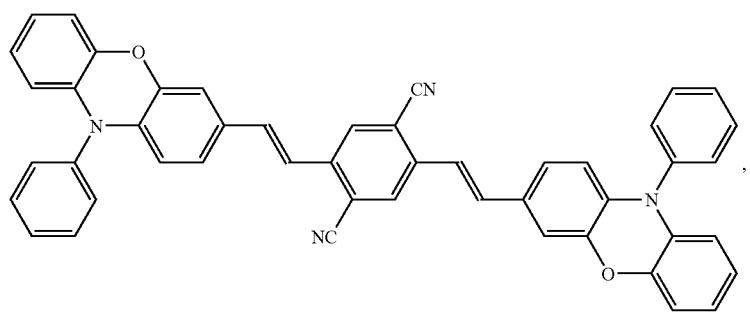
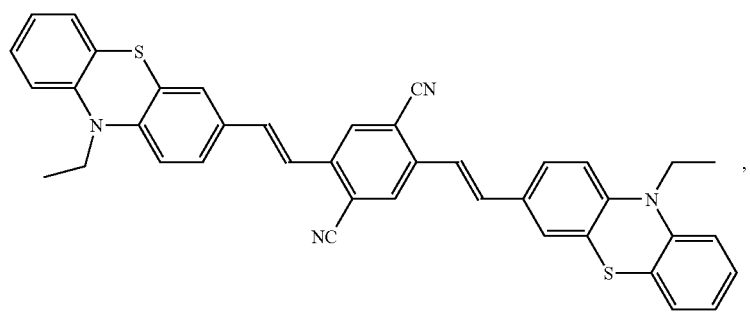

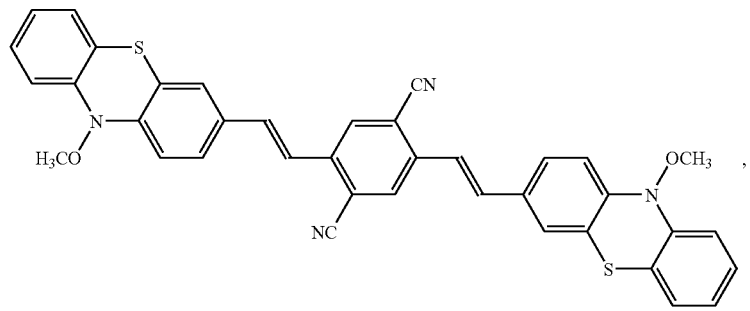
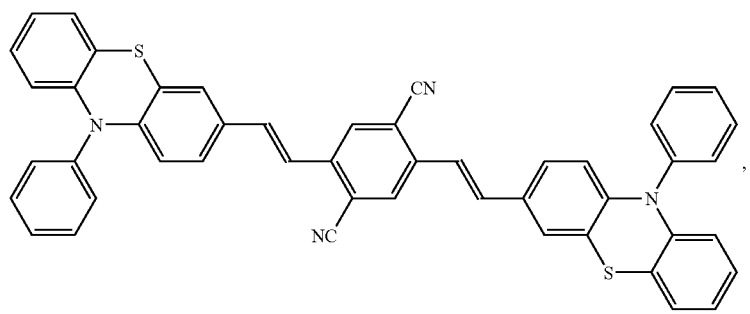
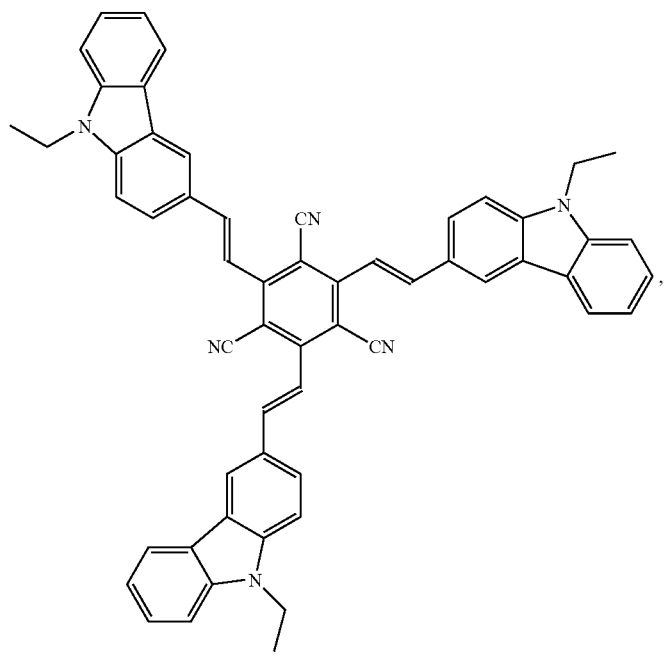

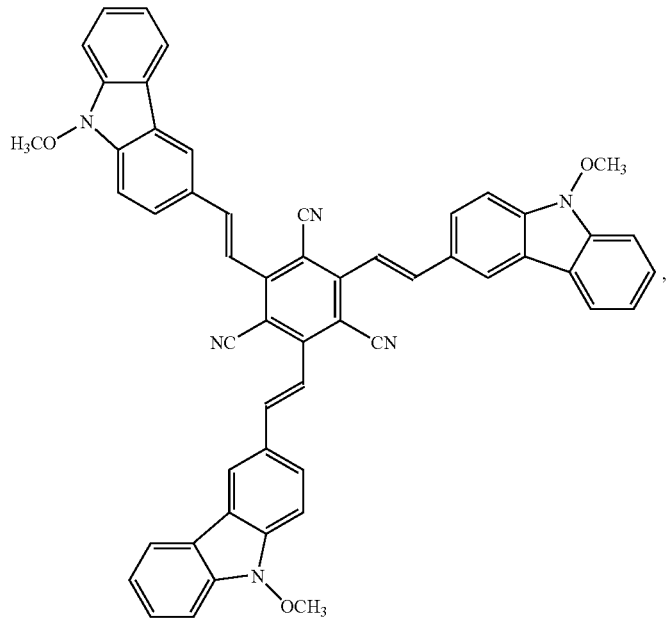
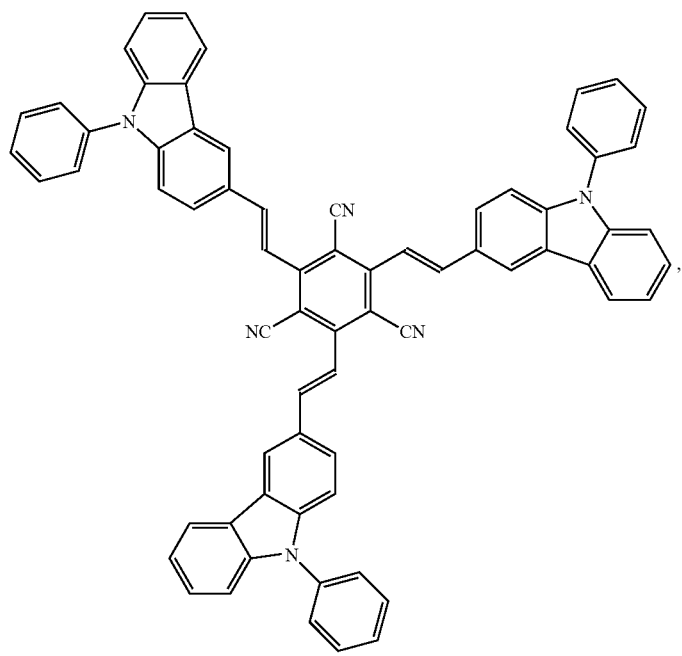

-continued
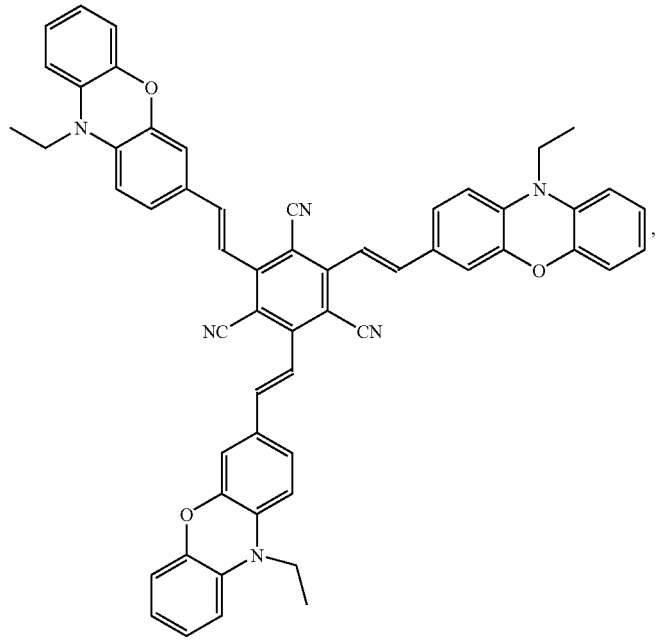
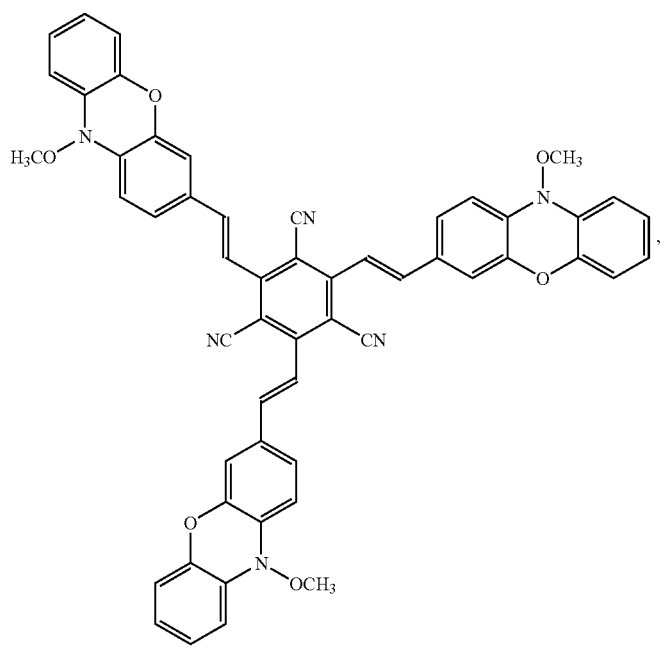

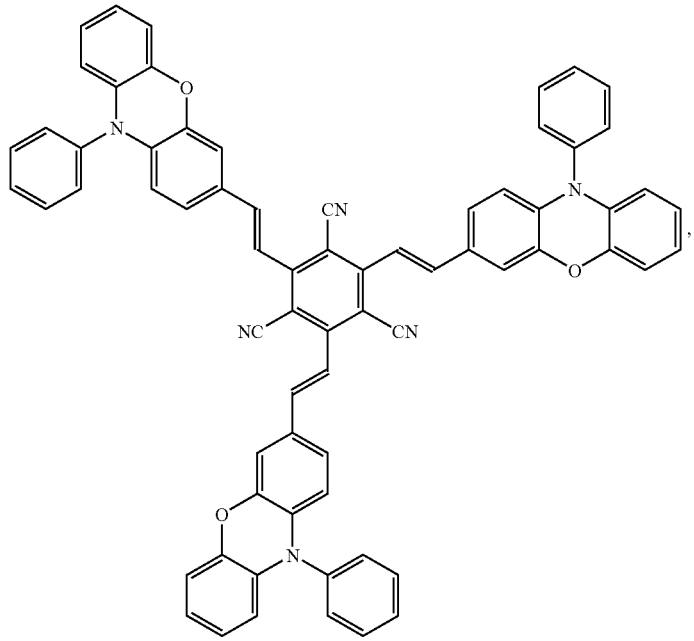
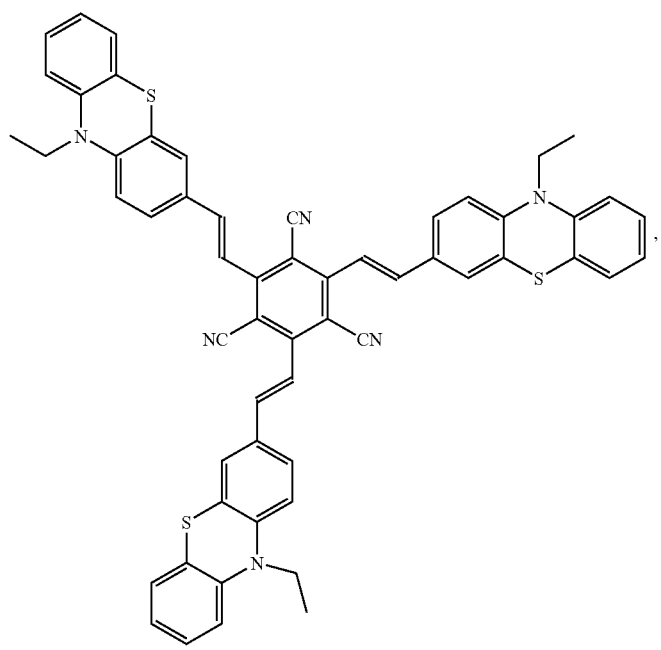

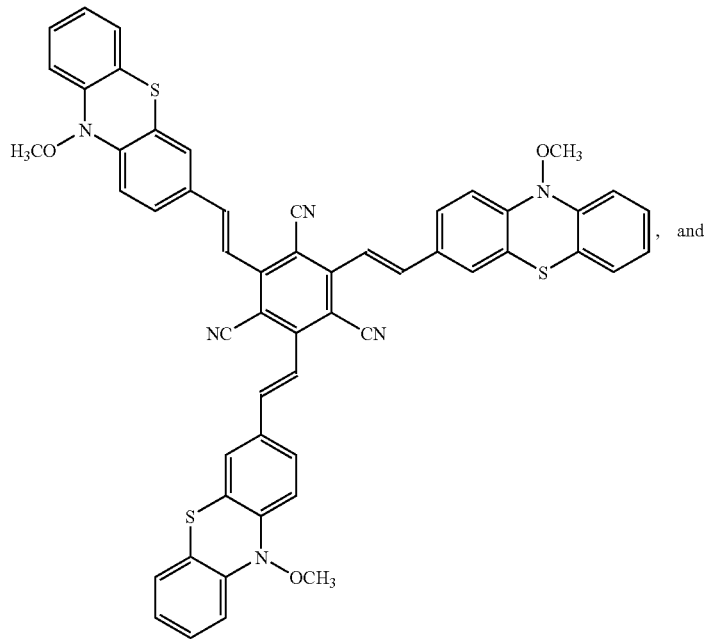
, and
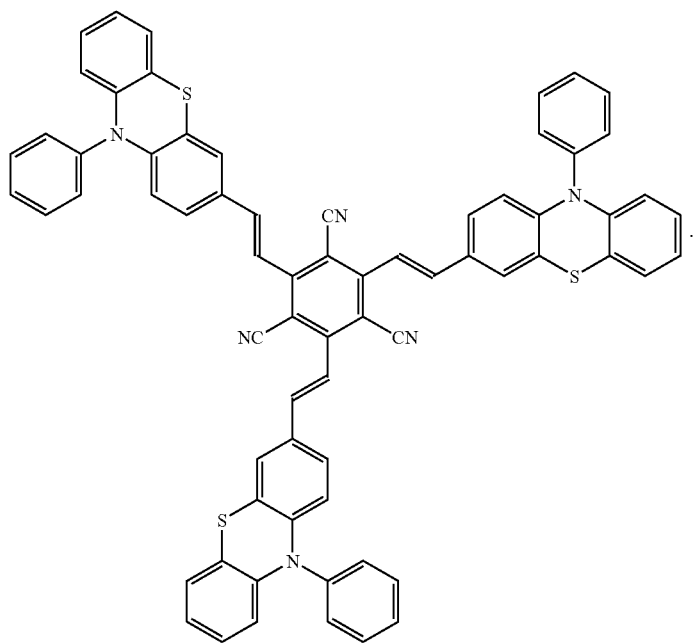
.

3. An organic electroluminescent device having one or more organic thin layers formed between a first electrode and a second electrode, wherein at least any one layer of the organic thin layers comprises one or more compounds represented by the following formula (1):

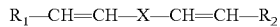

wherein,

X is

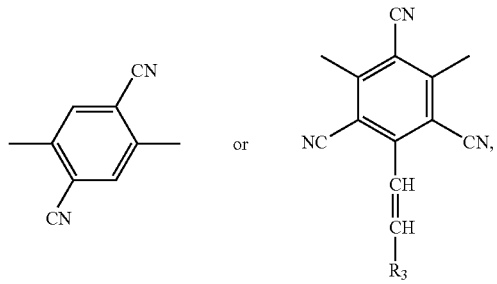

$R_1$, $R_2$ and $R_3$ each are independently formula (2), formula (3), or formula (4) or formula (5), with the proviso that $R_1$ and $R_2$ each are not formula (5) when x is 1,4-dicyanophenyl,

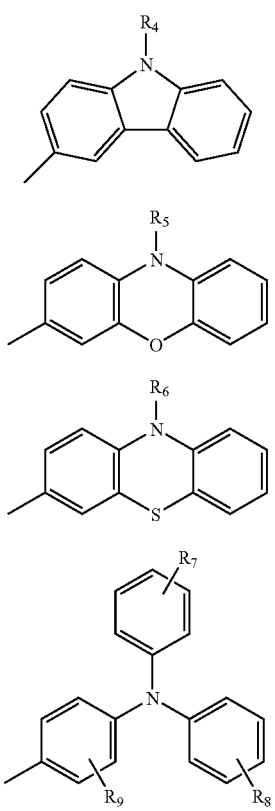

wherein $R_4$, $R_5$, $R_6$, $R_7$, $R_8$ and $R_9$ each are independently a hydrogen atom, a halogen group, a substituted or unsubstituted alkoxy group, a substituted or unsubstituted alkyl group, or a substituted or unsubstituted allyl group.

4. The organic electroluminescent device according to claim 3, wherein the organic thin layer comprises one or more layers selected from the group consisting of a hole transport layer, an emission layer, a hole blocking layer, an electron transport layer, and an electron injection layer.

5. The organic electroluminescent device according to claim 4, wherein at least one or more compounds represented by the formula (1):

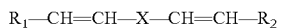

wherein,

X is

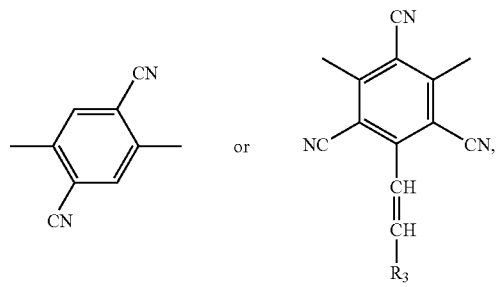

$R_1$, $R_2$ and $R_3$ each are independently formula (2), formula (3), or formula (4) or formula (5), with the proviso that $R_1$ and $R_2$ each are not formula (5) when x is 1,4-dicyanophenyl,

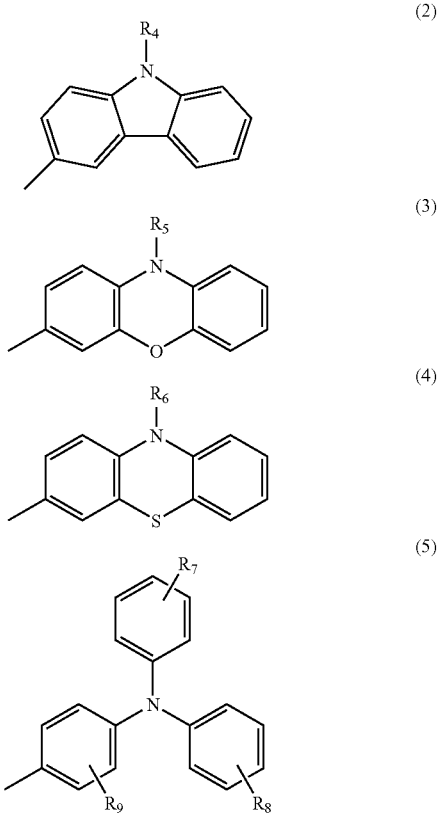

wherein, $R_4$, $R_5$, $R_6$, $R_7$, $R_8$ and $R_9$ each are independently a hydrogen atom, a halogen group, a substituted or unsubstituted alkoxy group, a substituted or unsubstituted alkyl group, or a substituted or unsubstituted allyl group are used as dopant of the emission layer.

6. The organic electroluminescent device according to claim 4, wherein at least one or more compounds represented by the formula (1):

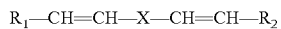

wherein,
X is

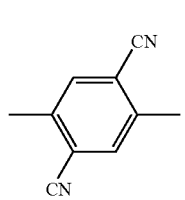 or 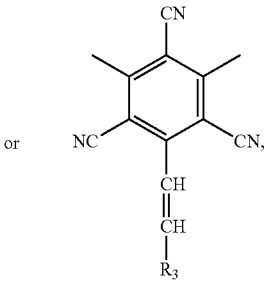

$R_1$, $R_2$ and $R_3$ each are independently formula (2), formula (3), or formula (4) or formula (5), with the proviso that $R_1$ and $R_2$ each are not formula (5) when x is 1,4-dicyanophenyl,

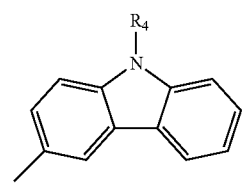 (2)

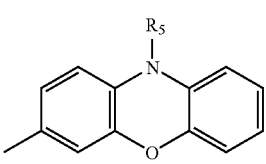 (3)

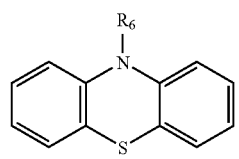 (4)

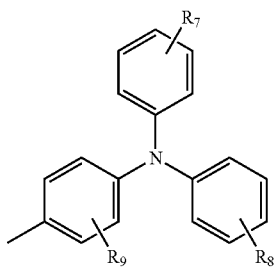 (5)

wherein,
$R_4$, $R_5$, $R_6$, $R_7$, $R_8$ and $R_9$ each are independently a hydrogen atom, a halogen group, a substituted or unsubstituted alkoxy group, a substituted or unsubstituted alkyl group, or a substituted or unsubstituted allyl group are used as host of the emission layer.

7. The organic electroluminescent device according to claim 4, wherein at least one or more compounds represented by the formula (1):

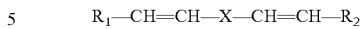

wherein,
X is

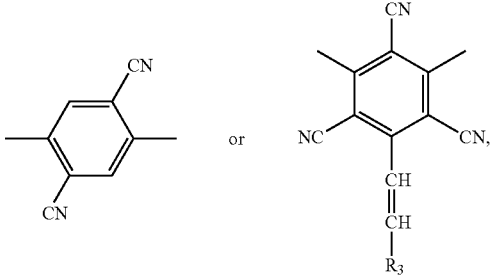

$R_1$, $R_2$ and $R_3$ each are independently formula (2), formula (3), or formula (4) or formula (5), with the proviso that $R_1$ and $R_2$ each are not formula (5) when x is 1,4-dicyanophenyl,

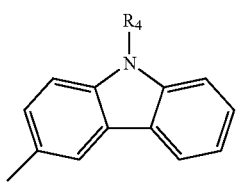 (2)

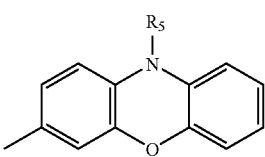 (3)

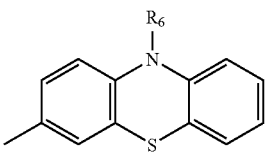 (4)

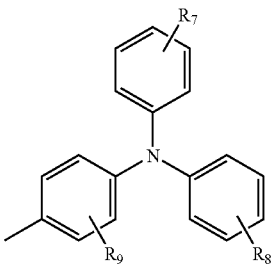 (5)

wherein,
$R_4$, $R_5$, $R_6$, $R_7$, $R_8$ and R9 each are independently a hydrogen atom, a halogen group, a substituted or unsubstituted alkoxy group, a substituted or unsubstituted alkyl group, or a substituted or unsubstituted allyl group are used as both host and dopant of the emission layer.

* * * * *